US008592500B2

(12) United States Patent
Grenness

(10) Patent No.: US 8,592,500 B2
(45) Date of Patent: Nov. 26, 2013

(54) OPTICAL COMPOSITION FOR IMPRESSIONS OR REPLICAS OF SMALL OBJECTS

(76) Inventor: Malcolm Grenness, Hobart (AU)

( * ) Notice: Subject to any disclaimer, the term of this patent is extended or adjusted under 35 U.S.C. 154(b) by 504 days.

(21) Appl. No.: 11/787,006

(22) Filed: Apr. 13, 2007

(65) Prior Publication Data

US 2008/0057479 A1    Mar. 6, 2008

Related U.S. Application Data

(63) Continuation-in-part of application No. PCT/AU2005/001593, filed on Oct. 14, 2005.

(30) Foreign Application Priority Data

Oct. 14, 2004  (AU) ............................... 2004905992

(51) Int. Cl.
*A61K 6/10* (2006.01)
*A61C 9/00* (2006.01)
*C08K 5/22* (2006.01)

(52) U.S. Cl.
USPC ............................ 523/109; 433/214; 524/430

(58) Field of Classification Search
USPC .................................. 433/214; 523/430, 109
See application file for complete search history.

(56) References Cited

U.S. PATENT DOCUMENTS

| 2,970,127 | A | * | 1/1961 | Slayter et al. | 428/221 |
| 3,454,517 | A | * | 7/1969 | Neros et al. | 524/134 |
| 3,484,262 | A | * | 12/1969 | Hahn | 428/402 |
| 3,607,349 | A | * | 9/1971 | Dereich | 427/266 |
| 4,132,563 | A | * | 1/1979 | Burke et al. | 523/200 |
| 4,347,174 | A | * | 8/1982 | Nagase et al. | 523/116 |
| 5,362,769 | A | * | 11/1994 | Waller et al. | 523/116 |
| 5,698,610 | A | * | 12/1997 | Futami et al. | 523/109 |
| 6,201,038 | B1 | * | 3/2001 | Waller et al. | 523/109 |
| 6,201,057 | B1 | * | 3/2001 | Porter | 524/501 |
| 7,393,620 | B2 | * | 7/2008 | Kim | 430/108.11 |
| 2002/0071783 | A1 | * | 6/2002 | Fader et al. | 422/13 |
| 2003/0142863 | A1 | | 7/2003 | Massen | |
| 2003/0162150 | A1 | | 8/2003 | Engelbrecht | |
| 2006/0068311 | A1 | * | 3/2006 | Kim | 430/108.11 |
| 2007/0036900 | A1 | * | 2/2007 | Liu | 427/372.2 |
| 2008/0145820 | A1 | * | 6/2008 | Karmaker et al. | 433/220 |

FOREIGN PATENT DOCUMENTS

JP          404342512 A  *  11/1992

* cited by examiner

*Primary Examiner* — Tae H Yoon

(74) *Attorney, Agent, or Firm* — Christensen O'Connor Johnson Kindness PLLC

(57) ABSTRACT

A composition, apparatus and method for preparing a 3-D impression or replica of small objects. It is particularly aimed at the dental field and provides improved optical texture of an impression or replica of a small object to enable imaging by photogrammetry. The composition comprises a liquid curable polymer; macroparticles having a size greater than about 1 μm in diameter and microparticles present in a size range of less than about 1 μm such that the macroparticles and microparticles are present in a ratio in the range of between 5:1 and 15:1 (by volume); wherein the impression or replica formed from the composition has a surface particle distribution effective to allow imaging by photogrammetry.

5 Claims, 4 Drawing Sheets

OPTICAL COMPOSITION FOR IMPRESSIONS OR REPLICAS OF SMALL OBJECTS

This application is a continuation of PCT Application PCT/AU2005/001593, filed on Oct. 14, 2005, which was a continuation of Australian patent application Ser. No. 2004905992, filed on Oct. 14, 2004.

FIELD OF INVENTION

This invention relates to a composition, apparatus and method for preparing a 3-D impression or replica of small objects. It is particularly aimed at the dental field but is not limited thereto.

BACKGROUND OF THE INVENTION

Mapping or 3D-imaging of small objects such as teeth or fossils and artifacts and the like is important to enable obtainment of constructional data which is necessary for special analysis and computer-controlled manufacture of a replacement such as a tooth replacement as an example.

Quantitative measurement systems are traditionally classified according to the principle by which data are collected, such as contact or non-contact, surface topography or silhouette tracing. However, with the advent of digital technology, whatever the method of data collection, data are reduced to 2D or 3D coordinate data. The data can then be manipulated depending on the requirements for imaging or further processing and analysis.

Coordinate points can be taken as single predetermined points or at random, a collection of points along a profile, along contours and/or around image outlines. So, for example, where a silhouette of an object is hand traced, photographed or captured with a video camera, the silhouette line is sampled at regular intervals to extract 2D coordinates. The third coordinate can be derived from the position of the silhouette within the object. This method may require destruction of the object or replica being measured.

Laser-stripe scanning/profiling results in the recording of the stripe digitally. The stripe is then sampled or broken up into its component parts to extract 2D data. Once again, the stacking of many stripes leads to the determination of 3D coordinates. While the two techniques may appear quite different, basic principles remain much the same. Quantitative determination of tooth and lesion geometry has been performed using variations on these principles with varying accuracies and precisions, and have been performed directly on teeth in the mouth, on elastomeric impression negatives, or on positive replicas of teeth poured from elastomeric impressions.

Laboratory based profilometry of tooth replicas with contact stylus systems has been the norm since the early 1980s. Precisions in the order of a few micrometers have been commonly reported by the middle 1990s (e.g. Lee I K, DeLong R, Pintado M R, Malik R. Evaluation of factors affecting the accuracy of impressions using quantitative surface analysis. Operative Dent. 1995; 20:246-52.) However in order to gain high accuracy only one tooth can be profiled at a time, the surface of both tooth replica and stylus tip degrade with time leading to reduced accuracy. Tooth replicas are specially prepared and mounted on a rotating turntable. Full measurement of the geometry of a tooth may take several hours. Contact stylus systems are available for the measurement of larger objects comprising full dental arches however they yield lower accuracy and are unable to measure surface points at the steep angles leading to areas between teeth.

Laser scanning/profiling of replicas has become more common since the late 1990s. Precision in the range of 1 to 1O µm have been reported (e.g. Mehl A, Gloger W, Kunzelmann K-h, Hickel. R. A New Method of 3D Device for Detection of Wear. J. Dent.-Res. 1997; 76(11): 1799-807.). This method is similar to contact stylus profiling with the laser stripe replacing the contact stylus. It has the significant advantage of being very fast, with surface topography being recorded in a matter of seconds to minutes. However this "method typically requires the preparation of individual tooth replicas mounted onto a rotating turntable.

An alternative field to profilometry is that of machine vision where the projection of multiple stripes onto a surface and recording the scheme on one image. Machine vision involves three primary components—a laser light source, video camera and a computer. Typically a laser light grid is projected onto a light strip or planar substrate parallel to the plane of a sensor/CCD/film and the resulting light pattern is recorded as a template. The light pattern is then projected onto a scene. Analysis of the difference/distortion of the light pattern between the template and scene is analyzed by computer software to quantify the 3D profile of x, y and z co-ordinates of each point of the projected scene. There are however limits to the resolution of the light pattern that can be projected, leading to limitations on the grid density that can be determined. This approach is for practical purposes best suited to machined objects consisting of planes, circles and arcs for which only a small number of points is required to mathematically describe the geometry of that part of the surface. Boundaries between geometric surfaces can be easily and accurately interpolated. An application of this is quality control in the manufacture of aeroplane wings, where the entire assembled wing is wheeled into a hanger and photographed with a dozen cameras from different angles, instantaneously, and the geometry of the wing checked against a template. This type of technique has not been considered adequate for mapping of biological surfaces due to their irregular nature and consequent need for dense point determination.

Machine vision using direct optical 3-D surveying techniques have been applied in clinical practice on tooth replicas (models formed from an impression negative) and directly in the mouth of a patient where the tooth surface has been machined/drilled to regular shape in preparation to receive a machined restoration/filling. A French system based on the work of physician Dr. Duret is known to operate with a laser-triangulation method for the point-by-point measurement of the distance between a tooth surface and an optical probe, in which the optical probe is inserted into the oral cavity of the patient. By carrying out either a point-by-point distance measurement or through scanning by projecting a laser along a line, relative height coordinates of a scanned object can be obtained along the scanning line. CCD-scanning line sensors are ordinarily employed as optical pick-ups or receivers enabling pick up of point rasters.

A Swiss system utilized by the company of BRAINS, Brandistini Instruments, Switzerland, designated by the description CEREC, operate. in accordance with a light-section technique in which a single line or dash of light or parallel grid consisting of dashes or lines of light are projected onto a surface and observed under a parallax-angle with a two-dimensional camera. From the curvature of lines of the light-section relative heights can be computed. A variant of this technique referred to as the 'phase-shift' method is known which employs an interferometrically-produced light grid with sinusoidal brightness modulation in contrast with the binary light-sections. Through a pick-up or recording of an object at a plurality of positions for the phase location of this grid, there can be obtained in a significantly higher point density of height values and any disturbing influences, such as non-constant background brightness and fluctuating stripe or line contrast caused by localized fluctuations in reflection, which can be mathematically eliminated.

The structured light technique utilized by the CEREC system is the only intra-oral method currently available for tooth mapping. It was specifically designed for the mapping of prepared tooth cavities and has not been used for general tooth mapping. Its utility in this regard is unknown. Its reported accuracy of 25 μm for mapping and 40 μm error associated with the need to apply an opaque powder to the tooth surface intra-orally is inferior to that of laser or contact mapping and would appear inadequate for the monitoring of tooth wear. However, as a direct method, it is considerably faster and more convenient than other methods.

A further system proposed by Massen; Robert (Radolfzell, D E); Gassier; Joachim (Constance, D E), U.S. Pat. No. 5,372,502 is an optical three-dimensional measuring probe which is utilized to generate a three-dimensional image of a single tooth or a group of teeth within the oral cavity of a patient. The measuring probe projects a particular pattern onto the single tooth or group of teeth which is/are to be surveyed. The particular pattern projected can be, for example, a series of parallel stripes. This projected pattern of stripes is distorted by the tooth or teeth which is/are to be measured due to variations in height. Basically, the pattern is distorted by the tooth or teeth which is/are to be measured in that the individual stripes fall on sections of the tooth which are of different height or fall on different teeth which are different height. The distorted pattern is reflected back towards the measuring probe, which captures the distorted pattern and transmits it ultimately to a computer. Through a comparison between the undistorted pattern projected by the probe and the distorted pattern reflected from the specific area within the oral cavity, information with respect to the topography of the tooth or teeth is obtained. In order to preclude ambiguities in this topographical information and to increase the precision of the measurement, the surveying procedure is repeated a number of times whereby the pattern, which is projected against the tooth or teeth, is always varied. Accordingly, the distorted pattern, which is captured by the measuring probe, will also vary; however, each iteration provides refinement of the topography. This approach describes a further refinement to the Cerec system. The system may yield some technical improvements however they would appear to be of limited practicality.

A literature review of the techniques to measure tooth wear and erosion (Azzopardi A, Bartlett D W, Watson T M, Smith G N. A Literature Review of the Techniques to Measure Tooth Wear and Erosion. Eur. J. Prosthodont. Rest. Dent. 2000; 8(3):93-97) concluded that profilometry remained a technique limited to the laboratory and that there was a need for a simple, reliable technique. No technique has been used sufficiently extensively clinically to merit widespread application.

During the 1970's and early 1980's, an alternative approach using photogrammetry techniques was investigated by several authors and produced accuracy of 10 μm in limited laboratory studies (Clarke C E, Flinn R M, Atkinson K B, Wickens E H. The measurement Comparison of Tooth Shape Using Photogrammetry; Photogrammetric Record 1974; 8(44):217-21; Chiat B., The shapes of small pebbles; Photogrammetric Record 1977; 9(49):77-82. Adams L P. The use of a non-metric camera for very short-range dental stereophotogrammetry. Photogrammetric, Record 1978; 9(51):405-14; Lamb RD, McGarrah H E, Eick J D. Close-range photogrammetry with computer interface in dental research. Photogrammetric Engineering and Remote Sensing 1987; 53(12):1685-89.).

The majority of work on teeth has been conducted with microscopes, however the applicant has come to realize that work on the cornea with macro-lens cameras (Osborn J E. Stereophotogrammetric mapping of the anterior surface of the human cornea. Int Arch photogram and remote sensing 1996; 31 (Part B5):443-49) may be suited to imaging teeth both clinically and in the laboratory on replicas. While photogrammetry has the advantage of capturing images quickly for later processing at a convenient time, Clarke et al (1974) noted that an experienced operator could record 1000 points in 4 hours. This very slow recording time for surface measurement when compared with modern laser scanning where many thousands of points can be recorded in a matter of seconds has rendered photogrammetric method impractical for high-resolution measurement of small objects.

Photogrammetry applies techniques, which are used and were principally developed for land mapping based on taking measurements off aerial photographs. Two kinds of photograph are used in photogrammetry, aerial and terrestrial. In aerial photogrammetry a sensor location (camera) is "remote" (in an aeroplane) from an object or scene. In this application there is a need for the calculation of a large number of unknown parameters in order to build an accurate model of the terrain below. Photogrammetry relies on the presence of sufficient natural features on the surface of a scene to perform triangulation and height determination. It has the principal advantage of fast and convenient image acquisition using relatively inexpensive camera equipment with the possibility of images being processed with photogrammetric workstation software at a later time when a topographical map is required. So images can be recorded and stored for years if necessary before photogrammetric processing is performed and high quality topographic measurement is performed. Alternatively, a calibrated stereometric camera and automated software that performs establishment of corresponding points in the images (Image Matching), computation of their 3D coordinates; and generation of a surface model, may be used to generate a topographical map within a matter of seconds. Many attempts to extract 3D coordinated data from small objects, especially teeth, have been limited to extracting 3D coordinated data from the outlines of particular features and have focused on the theoretical accuracy and precision that can be achieved, but have fallen well short in applicability due to the lack of natural features present on the entire surface. This characteristic is referred to as "optical texture".

There has been the advent of higher resolution digital cameras and automatic processing (e.g. Mitchell H L, Kniest H T, Oh W J. Digital photogrammetry and microscope photographs. Photogrammetric Record, 1999; 16(94):695-704.). It could be presumed that this makes developing the photogrammetric approach to laboratory and/or intra-oral mapping of teeth a real possibility. However, an attempt by Mitchell et al to use digital photogrammetry to map a tooth replica was unsuccessful due to a lack of radiometric (optical) texture and to date there are no reports of successful stereo photogrammetric mapping of complete tooth surfaces, either natural, impression negatives or replicas.

Materials which are frequently used for impression negatives and in particular replicas of small objects fall into three broad categories: mineral e.g. gypsum products; polymers e.g. epoxy, urethane, styrene etc; and metals.

Where die materials are to be mapped with a mechanical probe profiler, the material must have sufficient rigidity to resist deformation and excessive abrasion during contact; type IV diestones and metals are typically used for this purpose. Where die materials are mapped with a non-contact laser profiler or structured light projection system, the material must be sufficiently optically dense so that light is reflected from the surface of the die. This is not a problem with gypsum products, but polymers, which may be naturally clear, must be coloured sufficiently densely so that no light is reflected from below the surface resulting in excessive light scatter. Recently 3M has produced an experimental polyvinyl siloxane elastomeric material known as 'Digisil' which has been coloured with the aim of improving the surface reflection of laser profilometry equipment (DeLong R, Heinzen M, Hodges J S, Ko C C, Douglas W H. Accuracy of a system for creating 3D computer models of dental arches. J Dent Res. 2003; 82(6):438-42.). The application of metal and paint films to replicas to enhance their surface properties in conjunction with contact stylus profiling has also been reported (Chadwick R G, Mitchell H L, Ward S. Evaluation of the accuracy and reproducibility of a replication technique for the manufacture of electroconductive replicas for use in qualitative clinical dental wear studies. J. Oral Rehabil. 2002; 29:540-45.). Die or model materials are known in the diagnosis and treatment of a dental condition. Indeed harden-able polymeric materials are used in a number of dental applications comprising composites, filling materials, restorations, cements, and adhesives. To date there appears to be no successful 3D-imaging of small objects by stereo photogrammetric mapping of objects from conventional die materials.

One recent attempt to provide images of small mammalian teeth has used a method in which a replica is created by mixing a fluorescent dye in a urethane polymer and imaging the replica with a confocal microscope. This method is however slow and requires the use of very expensive confocal imaging equipment (Evans A R, Harper I S, Sanson G D. Confocal imaging, visualisation and 3-D surface measurement of small mammalian teeth. J. Microsc. 2001; 204(2): 108-19.). Typically several images at lower magnifications need to be combined to map human teeth, with a slight reduction in accuracy. Computed tomography is in an early phase of study. Its future utility is uncertain.

It is to be understood that any discussion of prior art heretofore is not an admission that such art constitutes common general knowledge.

The invention aims to improve optical texture characteristics to allow structural and topographical mapping by photogrammetry.

The present invention therefore is to provide a composition with improved optical texture to allow imaging of impressions or replicas of small objects by photogrammetry.

A further object is to provide an alternative to existing techniques of imaging objects, which ameliorates one or more of the disadvantages of the prior art.

SUMMARY OF THE INVENTION

The invention accordingly provides a composition having improved optical texture for providing an impression or replica of a small object suitable for imaging by photogrammetry, the composition comprising: a liquid curable polymer; macroparticles having a size greater than about 1 μm in diameter and microparticles present in a size range of less than about 1 μm such that the macroparticles and microparticles are present in a ratio in the range of between 5:1 and 15:1 (by Volume); wherein the impression or replica formed from the composition has a surface particle distribution effective to allow imaging by photogrammetry.

The composition of the invention provides improved optical texture of an impression- or replica of a small object by optimizing the particle distribution/density at or close to the surface. The particle distribution/density at the surface of a textured impression or replica creates target features, which allows for automatic image matching by digital photogrammetric work-station software. This in turn enables generation of a surface model of small objects, which hitherto has not been possible with conventional impressions, or replicas of small objects. The target features at or close to the surface of a replica or impression produced from the inventive composition provides a scene from which triangulation and height measurements can be determined by the technique of photogrammetry. The increased distribution/density of particles at or adjacent to the surface also assists in minimizing sub-surface light scatter, which is attributable to translucent impressions or replicas. An impression of teeth, for example, formed from the present composition, in which optical texture is created at the surface of the impression, allows imaging or mapping of the impression by photogrammetry to be achieved in a similar amount of time as it takes for a conventional dental x-ray.

In a further aspect of the invention there is provided a method for manufacturing a replica of a small object which is suitable for imaging by photogrammetry, the method comprising forming a composition comprising a liquid curable polymer; macroparticles having a size greater than about 1 μm in diameter and microparticles present in a size range of less than about 1 μm such that the macroparticles and microparticles are present in a ratio in the range of between 5:1 and 15:1; pouring the composition into a shaped mould created from a negative impression of a small object and allowing to set so that the composition forms a replica of the shaped mould; and subjecting the replica to air abrasion wherein the replica has a particle size distribution at or close to its surface effective to create target spots to allow reproductive imaging by photogrammetry.

Digital photogrammetry methods of surface measurement have hitherto not been known or applied to small objects due to lack of optical texture at or close to the surface of the object. The composition of the present invention provides optical texture at or close to the surface of an impression or replica so that photogrammetry methods and software can be used as a surface modeling technique on such a small scale. One advantage of the present invention is that applying the technique to small objects such as snails, artifacts, teeth, biofilms, and other small objects, surface geometry of such objects can be mapped directly and changes in surface geometry can be detected over a period of time. As an example of the application mapping of impressions or replicas formed from the instant composition can enable clinical monitoring of tooth wear and development of surface defects.

The macroparticles can have a size distribution in the range of between about 100 and 200 μm in diameter. The particle size distribution at the surface of a replica or negative impression formed by the composition can range between 35 to 150 μm. A particle distribution/density within the range of between 35 to 150 μm provides a replica or an impression that allows optimal imaging although it is understood that other particle size distributions/densities are also suitable to enable adequate imaging by photogrammetry. The particles can have a regular or irregular geometry. The micro particles can be tinted or naturally coloured pigments to provide contrast to the macro-particles. The advantage of colouring is that the composition may be rendered opaque so that only the surface of the object is imaged. Generally the liquid curable resin component is translucent. Hence if only macro-particles were present in the resin component, parts of the surface of an impression or replica, between adjacent surface particles, would appear translucent potentially creating errors in mapping.

The macro and micro-particles can be selected from polymer-based particles, although it is understood that particles are not limited to polymers. For instance metallic particles can be used such as but not limited to metallic filings and titanium dioxide. The visual effect of creating a surface texture by adding macro particles and micro particles is generally not readily apparent when judged by an unaided eye. The surface texture can however be viewed when photographed with a high resolution camera and the image pixelated. At this level of surface texture and particle density, photogrammetry software can analyze the resulting digital image.

The liquid curable polymers can be selected from epoxy resins; polyvinylsiloxane(s); styrene; acrylates; urethanes; and the like settable (thermoplastic or thermosetting) resinous materials.

The macro- and micro-particles can be insoluble in the liquid curable polymer. The characteristic of insolubility helps maintain the integrity of particle size within the composition. The mass of particles needs to be similar to the polymer to help prevent the particles separating or settling out.

In a further aspect of the invention there is provided a composition having improved optical texture for providing an impression or replica of a small object suitable for imaging by photogrammetry, the composition comprising: a liquid curable polymer; macroparticles having a size distribution ranging between about 100 µm and 200 µm in diameter and microparticles having a size less than or equal to 1 µm such that the macroparticles and microparticles are present in a ratio in the range of between 5:1 and 15:1; wherein the impression or replica formed from the composition has a particle size distribution at or close to its surface ranging between about 35 µm to 150 µm to create target spots for enabling imaging by photogrammetry. These target spots are provided by the macroparticles and microparticles, and/or voids or air bubbles resident in the cured polymer.

The target spots ranging between about 35 µm and 150 µm at or close to the surface of an impression or replica can be readily photographed by high resolution charged couple device or other imaging equipment. Subsequently the photographic image can be automatically image matched with digital photogrammetric work-station software to produce high density, high resolution surface models of small irregular shaped objects.

In yet a further aspect of the invention there is provided a replica or impression of a small object suitable for imaging by photogrammetry, the replica or impression being formed from a composition comprising: a liquid curable polymer; macroparticles having a size greater than about 1 µm in diameter and microparticles present in a size range of less than about 1 µm such that the macroparticles and microparticles are present in a ratio in the range of between 5:1 and 15:1; wherein the replica or impression has the macro-particles and micro-particles embedded at or close to its surface forming an irregular surface structure which can be mapped by photogrammetry.

The interaction between the particles within the liquid matrix of curable polymer creates an irregular surface appearance. The irregular surface appearance provides an array of irregular surface targets that allows contoured mapping of the surface of the object by photogrammetry. The present invention provides an indirect means of surface mapping.

Prior art attempts to use photogrammetry techniques for mapping of teeth has suffered from the lack of recognizable targets on the tooth surface which is required for triangulation and height determination. The spatial distribution of particles at or close to the surface of a replica or impression produced from the instant composition overcomes prior art difficulties and allows the adaptation of photogrammetry methods to map irregular-shaped small objects, which hitherto has not been available.

In yet a further aspect of the invention there is described a replica or impression of a small irregular object formed from a composition in which macro-particles and micro-particles are added to a matrix of a liquid curable polymer in a ratio between 5:1 and 15:1, the macro-particles and micro-particles being combined in the resin matrix in a ratio between 1.5:1 and 3:1 (by volume) such that a maximum filler loading is obtained for the resin while the resin still remains sufficiently fluid; wherein the replica or impression has a surface on which the particles project outwardly from the matrix forming target points which enable mapping of the object by photogrammetry.

The novel features that are considered characteristic of the invention are set forth with particularity in the appended claims. The invention itself, however, both as to its structure and its operation together with the additional object and advantages thereof will best be understood from the following description of the preferred embodiment of the present invention when read in conjunction with the accompanying drawings. Unless specifically noted, it is intended that the words and phrases in the specification and claims be given the ordinary and accustomed meaning to those of ordinary skill in the applicable art or arts. If any other meaning is intended, the specification will specifically state that a special meaning is being applied to a word or phrase. Likewise, the use of the words "function" or "means" in the Description of Preferred Embodiments is not intended to indicate a desire to invoke the special provision of 35 U.S.C. §112, paragraph 6 to define the invention. To the contrary, if the provisions of 35 U.S.C. §112, paragraph 6, are sought to be invoked to define the invention(s), the claims will specifically state the phrases "means for" or "step for" and a function, without also reciting in such phrases any structure, material, or act in support of the function. Even when the claims recite a "means for" or "step for" performing a function, if they also recite any structure, material or acts in support of that means of step, then the intention is not to invoke the provisions of 35 U.S.C. §112, paragraph 6. Moreover, even if the provisions of 35 U.S.C. §112, paragraph 6, are invoked to define the inventions, it is intended that the inventions not be limited only to the specific structure, material or acts that are described in the preferred embodiments, but in addition, include any and all structures, materials or acts that perform the claimed function, along with any and all known or later-developed equivalent structures, materials or acts for performing the claimed function.

BRIEF DESCRIPTION OF THE DRAWINGS

Specific embodiments in accordance with this invention will now be described by way of illustration only with reference to the accompanying drawings wherein.

DESCRIPTION OF THE PREFERRED EMBODIMENT

The preferred embodiment will be described with reference to the following examples:

Example 1

Creation of a replica from a composition containing an Epoxy Die material according to the present invention.

In this example a replica or negative impression of an object such as an artifact, tooth or test object is obtained by firstly creating a preliminary (negative) impression of the object. The preliminary impression is produced by conventional means to create a die having a mould space therein. A positive (replica) is subsequently obtained by loading the mould space with a liquid composition containing (a) a two-pack epoxy casting resin; (b) macro-particles of polymeric material having a particle size ranging between about 100 to 200 μm in diameter; (c) micro-particles comprising titanium dioxide; wherein (d) the ratio of polymer particles to titanium dioxide particles is 10:1 (by volume).

The polymer particles and titanium dioxide are pre-mixed in a ratio of 10:1 in a mortar and pestle to ensure that there are no lumps or particles larger than 200 μm. The casting resin is mixed according to the manufacturer's instruction in a ratio of base to catalyst of 5:1. The premixed particles are added to the casting resin in a ratio of 1.5:1 (by volume) such that a maximum filler loading is obtained for the resin while the resin still remains sufficiently fluid. The composition is then transferred into the mould space and allowed to cure to create a replica of the preliminary impression.

Figure 1:
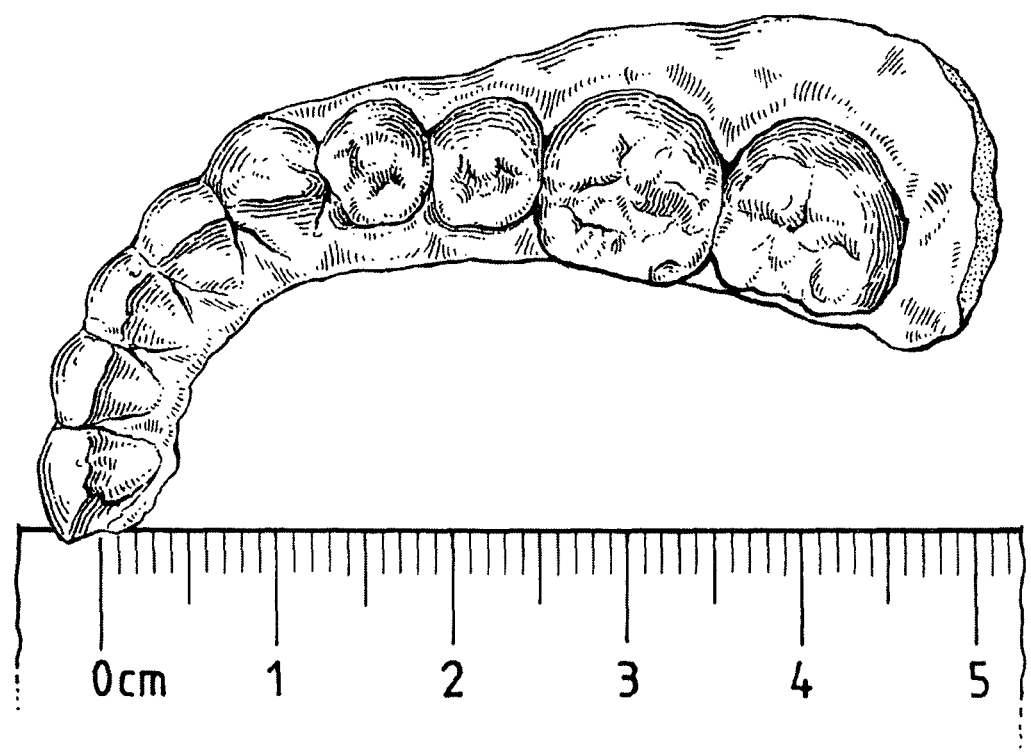
FIG. 1: is photographic view of a replica of a partial dental arch shown in elevation made in accordance with Example 1 positioned in relation to a millimeter scale ruler.

The replica is removed from the mould space and subjected to air abrasion with (i) aluminium oxide particles having a size ranging between 20 μm to 50 μm and (ii) a micro-etcher air brush to assist in removing plaque/sheen from the surface of the replica. Referring to FIG. 1 there is shown a replica of a part dental arch, which exhibits change in surface texture sufficient to allow accurate digital stereo mapping and imaging.

Figure 2:
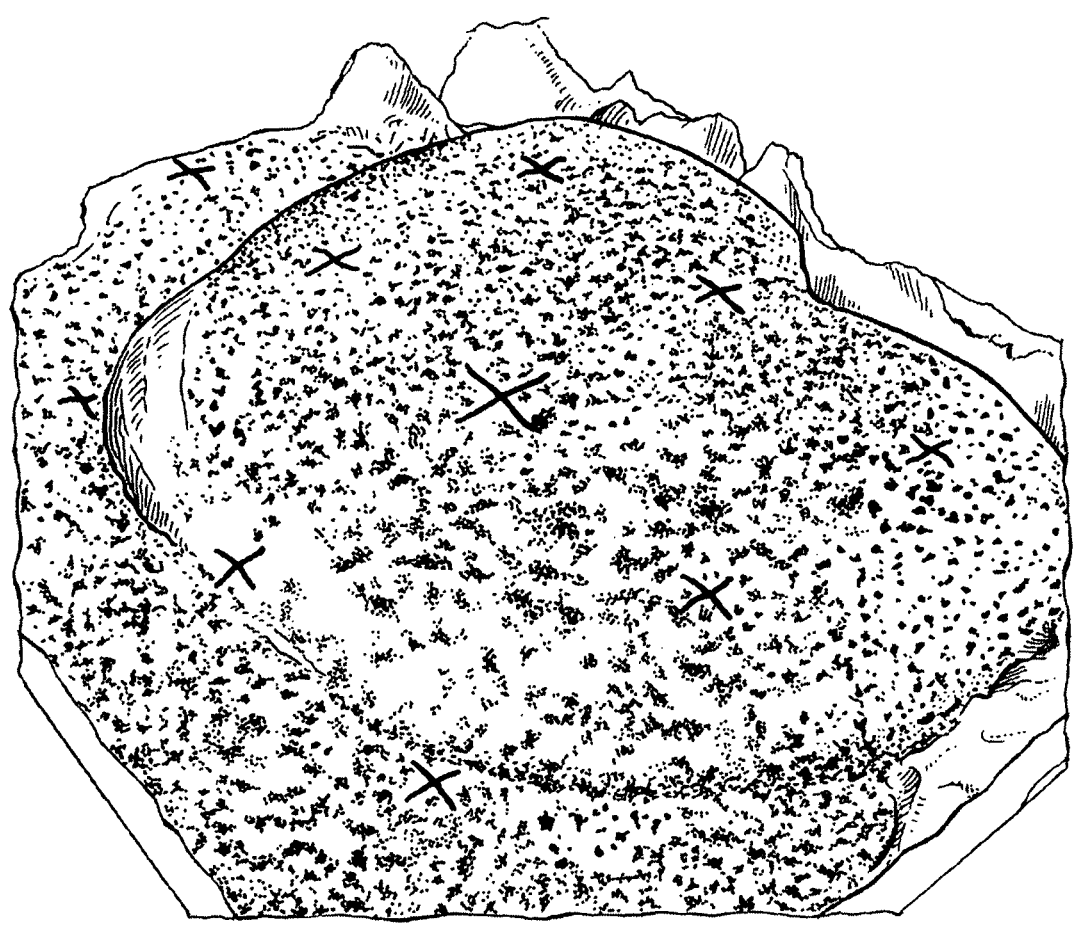
FIG. 2: is diagrammatic view of a digital image draped over a digital elevation model of a human lower molar with buccal surface tooth replica formed in accordance with Example 1.
Figure 3:
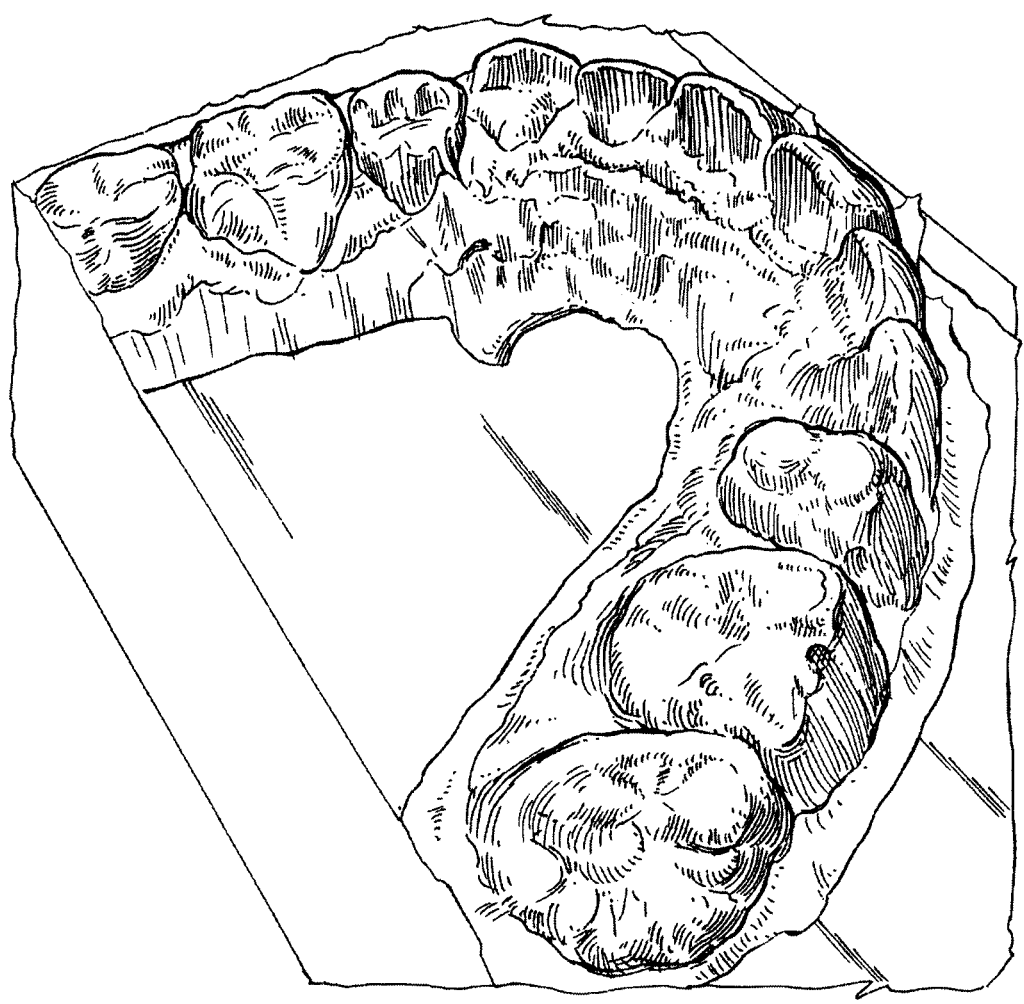
FIG. 3: is diagrammatic view of a digital image draped over a digital elevation model of occlusal and incisal surfaces of a maxillary dental arch.

The replica is subsequently photographed to generate stereo images of the surface of the replica or part of the surface required for mapping. FIGS. 2 and 3 show examples of digital images obtained from surface mapping of a replica such as that shown in FIG. 1. Generally this is performed with two images from a single camera, where the precise position of the camera is not required. Alternatively, two cameras can be used which may or may not be set in a precisely defined spatial arrangement. The two images are then processed with digital photogrammetric workstation software as is described by: Mitchell H L, Kniest H T, Oh W J. Digital photogrammetry and microscope photographs. Photogrammetric Record, 1999; 16(94):695-704.

Example 2

A Composition according to the present invention for use in creating an impression of a small object. In this example an impression is made of a tooth from a composition which includes (a) a two-part polyvinyl siloxane base resin; (b) macro-particles of polymeric material having a particle size ranging between about 100 to 200 μm in diameter; (c) micro-particles comprising titanium dioxide; and (d) a catalyst for initiating curing of the polymer base; wherein (e) the ratio of polymer particles to titanium dioxide particles is 10:1. The polymer macro-particles and titanium dioxide particles are added to the polymer base in the above ratio in an amount such that a maximum filler loading is obtained for the resin while the resin still remains sufficiently fluid. The catalyst is subsequently added in a minor amount and the resulting composition is poured against the tooth to form a positive impression.

Figure 4:
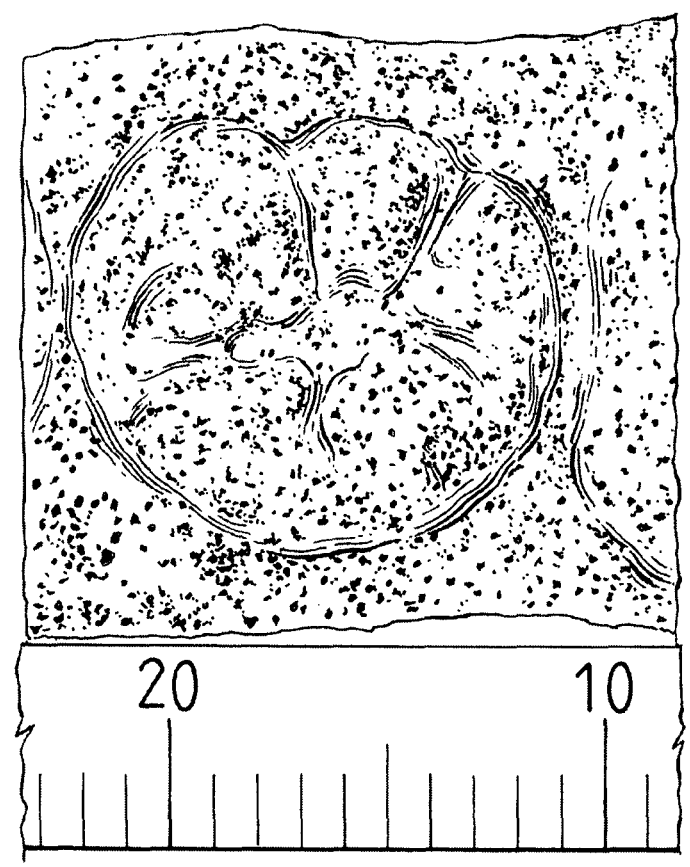
FIG. 4: is diagrammatic view of a digital image of a human upper molar, occlusal tooth surface impression formed in accordance with Example 2 positioned in relation to a millimeter scale; Detailed Description of the preferred embodiment.

The positive impression is subsequently photographed to generate stereo images of the surface of the impression or at least a surface of the tooth required for mapping. Referring to FIG. 4 there is shown a digital image of a tooth surface of a positive impression. Generally this is performed with two images from a single camera, where the precise position of the camera is not required. Alternatively two cameras can be used which may or may not be set in a precisely defined spatial arrangement. The two images are then processed with digital photogrammetric workstation software as is described by: Mitchell H L, Kniest H T, Oh W J. Digital photogrammetry and microscope photographs. Photogrammetric Record, 1999; 16(94):695-704.

Looking at the method of obtaining a photogrammetric image of an impression or replica of a small object in more detail, the method comprising manufacturing a negative impression or replica of an object or thin film on the surface of an object which is suitable for imaging and automatic image template matching, and digital elevation model (DEM) generation by digital photogrammetry. This requires the steps of providing a composition comprising a settable polymer of a mixture of macroparticles and microparticles in a predetermined ratio; —and applying the polymer to provide a distribution of high contrast and/or texture of particles at the surface of a negative impression or replica of an object forming an improved optical texture, or applying the composition consisting of a mixture of macroparticles and microparticles with the aid of a wetting agent to the surface of an object, in a thin film with improved optical texture.

In particular the composition includes a liquid curable polymer; macroparticles having a size greater than about 30 μm in diameter and microparticles present in a size range of less than about 5 μm such that the macroparticles and microparticles are present in a ratio in the range of between 5:1 and 15:1; adding the mixture of the macroparticles and microparticles in a predetermined ratio to a matrix of a liquid curable polymer in a ratio between 1.5:1 and 3:1 by volume. The composition is poured onto an object to create a negative impression or into a shaped mould created from a negative impression of an object to create a replica and allowing to set so that the composition forms a negative impression or replica of the object. The resulting replica or impression has a particle size distribution at or close to its surface effective to create a distribution at the surface of the impression or replica forming an improved optical texture of sufficient grey level and/or colour difference for imaging, automatic image template matching and 3D reconstruction by photogrammetry.

Two or more images of the surface of an object incorporating optical texture are acquired with a film camera and scanned to form a digital image, or acquired with digital camera/sensor. The images, consisting of pixel data, are orientated relative to the intrinsic parameters of the camera; and the location of the camera(s) at the time of image acquisition is determined relative to each other, and in relation to a defined coordinate system by computer software algorithm. Points of correspondence, common targets and/or groups of pixels are determined automatically between pairs of images by computer software algorithms and their pixel location determined and a digital elevation model (DEM) and/or digital 3D reconstruction of the surface is automatically generated by computer software algorithm. In one example all teeth of a 45-year-old male patient were polished with polishing paste and rubber cup. Upper and lower medium viscosity polyvinylsiloxane impressions (Reprosil; Dentsply International Inc., Miford, Del.) were taken in custom made impressions trays and full arch casts were poured in Type IV diestone (G C Fujirock E P; G C Europe N. V., Interleuvelaan, Belgium). The diestone casts were removed from the impressions and individual tooth replicas of teeth to be studied were poured with an epoxy die material (Daystar Australia P/L, Dandenong, Victoria, Australia) modified with the addition of white and coloured fillers. Tooth replicas were placed into a planar control grid of black film (Lithfilm; Agfa-Gevaert, Belgium) with eight transparent control points of 40 Dm diameter present at the right and left sides of the field of view (FIG. 1). The control grid was produced by exposing a grid of black spots of 250 um diameter on a 25 mm grid onto large format film with a vector plotter (Protel P/L, Hobart, Tasmania, Australia). The resulting photoplot was photographed with a process camera at a photographic reduction of approximately 6× onto film, which after developing was fixed to a 5-mm glass slab with adhesive (Photo Mount; 3M Australia P/L, Sydney, NSW, Australia). The x and y coordinates of the spots was measured with a stereo comparator (Stecometer; Carl Zeiss JENA, Jena, Germany) at a measurement accuracy of 2.5 Dm, and the z coordinates were given an arbitrary constant value.

For image acquisition/Interior Orientation the replicas were photographed with a 35-mm format semi-metric camera fitted with a 100-mm macro lens on extension bellows (Leica R5 Elcovision; Ernst Leitz Wetzlar GmbH, Wetzlar, Germany), achieving a magnification of 1.6×, and ASA 400 slide film (Sensa 400; Fuji Photo Film Co. Ltd., Tokyo, Japan) at convergence angles of approximately 5, 10, 15, 20 and 25 degrees. Processed film was scanned at a resolution of 10 Dm using a film scanner (Super Coolscan 4000; Nikon Corp., Japan). Camera calibration was performed using multiple convergence photography of a planar array and the method described by Heikkila.[57] Multistation photographs were taken with one view taken perpendicular to the calibration grid and four quadrant views taken at divergent angles of 7.5 and 10°. Between each view the lens aperture was opened to check to alignment of the calibration grid. A grid of 24 points of 40 Dm diameter and spaced at approximately 4 mm intervals was exposed onto film using the method described above and the coordinates of points on the array were measured using the stereo comparator as above. The array was photographed from five positions with standard multi-station geometry with the calibration software generating interior orientation parameters (radial and decentering lens distortion, focal length, principal point and a scaling factor).

For image matching and generation of 3D coordinate data digitized images of the tooth replicas were imported into the digital photogrammetric workstation station software (VirtuoZo, version 3.3; Supersoft Inc., Wuhan, Hubei, China), control point coordinates were entered in micrometers and camera calibration parameters including radial lens distortion data were entered. Interior orientation was performed using fiducial marks within the camera; exterior orientation was performed using up to eight control points and up to seven additional image matched points from the tooth replica. Epipolar resampling, automatic image matching, minor editing of matched points at the edges of the tooth stereo model and automatic generation of 3D coordinate digital terrain model (DTM) on a 50×50 Dm was performed. Coordinate data were imported into visualization and analysis software (Surfer, version 6.04; Golden Software Inc., Golden, Colo., USA). The effect of varying patch window size and match grid interval upon automatic image matching was examined for the convergence angle of 5°. DTMs were generated for each combination of patch size and grid interval and the same 1.5×2 mm section was extracted from the datasets and the standard deviation of the z-coordinates fitted to a plane was calculated.

Therefore the composition and method allow commercial digital photogrammetric software to be applied to convergent stereoscopic photography of human tooth replicas prepared to exhibit optical texture resulting in successful generation of 3D coordinate data.

The method can use semi-metric 35 mm format film camera but this results in time delays for film recessing and scanning. Also in stereophotogrammetric applications convergent geometries of 2 to 25 degrees are used to generate DEMs. The precision of DEMs is typically around 1O μm for convergences of 4 to 25 degrees decreasing to over 20 μm for convergence below 4 degrees. Currently available high resolution cameras of say 6.3 megapixel can be used which would yield images of the same resolution as the film images scanned at 1O μm pixel size with, the ability to accelerate and automate processing operations. The use of extension bellows can lead to instability of interior orientation parameters and resultant errors in the stereo models. However the design and application of a fixed focal length stereometric camera system would negate this instability and reduce or eliminate the requirement for interior and exterior orientation procedures an lead directly to image matching, epipolar resampling and DEM generation, all of which can be performed as automatic operations.

Finally it is to be understood that various alterations, modifications and or additions may be incorporated into the various constructions and arrangements of parts without departing from the spirit and ambit of the invention.

The preferred embodiment of the invention is described above in the Drawings and Description of Preferred Embodiments. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventor that the words and phrases in the specification and claims be given the ordinary and accustomed meanings to those of ordinary skill in the applicable art(s). The foregoing description of a preferred embodiment and best mode of the invention known to the applicant at the time of filing the application has been presented and is intended for the purposes of illustration and description. It is not intended to be exhaustive or to limit the invention to the precise form disclosed, and many modifications and variations are possible in the light of the above teachings. The embodiment was chosen and described in order to best explain the principles of the invention and its practical application and to enable others skilled in the art to best utilize the invention in various embodiments and with various modifications as are suited to the particular use contemplated.

What is claimed is:

1. A composition comprising:

polymeric macroparticles of a first color having a size greater than 30 μm in diameter and titanium dioxide microparticles of a second color having a size less than 5 μm in diameter combined with a liquid curable polymer, the macroparticles and the microparticles being insoluble in the liquid curable polymer;

wherein the composition provides an improved optical textured surface by providing a color contrast between the first color of the macroparticles and the second color of the microparticles, sufficient to be detected by automatic image template matching and digital elevation model (DEM) generation by digital photogrammetry;

wherein the macroparticles and microparticles are present in a ratio in the range of between 5:1 and 15:1;

wherein a mixture of the macroparticles and the microparticles is present in the composition in a predetermined ratio with the liquid curable polymer between 1.5:1 and 3:1 by volume; and wherein the mixture of polymeric macroparticles and titanium dioxide microparticles provides a polymeric macroparticle particle size distribution at the surface of a replica or negative impression formed by the composition in the range between 30 to 150 μm.

2. The composition of claim 1 wherein the polymeric macroparticles in the liquid curable polymer have a size distribution in the range of between 30 and 200 μm in diameter.

3. The composition of claim 1 wherein the polymeric macroparticles in the liquid curable polymer have a size distribution in the range of between 30 and 45 μm in diameter.

4. The composition of claim 1 wherein the mixture of polymeric macroparticles and titanium dioxide microparticles in the liquid curable polymer provide a polymeric macroparticle particle size distribution at the surface of a replica or negative impression formed by the composition in the range between 30 to 40 μm.

5. The composition of claim 1, wherein a hue, chroma or intensity of the first color is distinguishable from that of the second color to provide sufficient grey level and/or color difference, which allows for automatic image matching, and digital elevation model (DEM) generation by digital photogrammetry with respect to each other.

* * * * *